US010699405B2

(12) United States Patent  
Payne et al.

(10) Patent No.: US 10,699,405 B2  
(45) Date of Patent: Jun. 30, 2020

(54) SYSTEM AND METHOD FOR DXA TOMO-BASED FINITE ELEMENT ANALYSIS OF BONES

(71) Applicant: General Electric Company, Schenectady, NY (US)

(72) Inventors: Randall Payne, Madison, WI (US); Paul Markwardt, Madison, WI (US); Serge Muller, Buc (FR)

(73) Assignee: General Electric Company, Schenectady, NY (US)

( * ) Notice: Subject to any disclaimer, the term of this patent is extended or adjusted under 35 U.S.C. 154(b) by 299 days.

(21) Appl. No.: 15/720,738

(22) Filed: Sep. 29, 2017

(65) Prior Publication Data

US 2019/0102877 A1 Apr. 4, 2019

(51) Int. Cl.
*G06T 7/00* (2017.01)
*G06T 17/20* (2006.01)
(Continued)

(52) U.S. Cl.
CPC .......... *G06T 7/0012* (2013.01); *A61B 6/025* (2013.01); *A61B 6/032* (2013.01); *A61B 6/4452* (2013.01);
(Continued)

(58) Field of Classification Search
CPC ......... A61B 6/505; A61B 6/482; A61B 6/032; A61B 6/025; G06T 17/20; G06T 17/0012
See application file for complete search history.

(56) References Cited

U.S. PATENT DOCUMENTS 5,172,695 A * 12/1992 Cann .................. G16H 50/50  
600/407  
8,165,266 B2 * 4/2012 Wear .................... A61B 6/4042  
250/370.13  
(Continued)

FOREIGN PATENT DOCUMENTS

WO 2016129682 8/2016

OTHER PUBLICATIONS

Humbert, L. et al., "3D-DXA: Assessing the Femoral Shape, the Trabecular Macrostructure and the Cortex in 3D from DXA images", IEEE Transactions on Medical Imaging vol. 36, No. 1, Jan. 2017, pp. 27-39.

*Primary Examiner* — Yara B Green

(57) ABSTRACT

An imaging system utilizes 2D DXA images obtained in a tomographic imaging process or mode in order to provide more detailed information to the operator of the bone structure of the patient. The imaging system obtains multiple 2D DXA images at different angles with regard to the patient in a number of passes across the body of the patient. These 2D DXA images can then be utilized to reconstruct at least one 2D slice of the body of the patient, such as in a plane parallel to the plane of a patient support surface, such as a scanner table. The information provided by the tomographic reconstruction provides enhancements to the process of modifying a 3D FEA model associated to an already available set of tomographic reconstructed slices selected from the comparison with the current tomographic reconstructed slices. In this manner, the system and method provide a significant reduction in the error of the resulting modified 3D FEA model for review and analysis compared to a 2D approach.

16 Claims, 9 Drawing Sheets

(51) Int. Cl.
*A61B 6/00* (2006.01)
*A61B 6/03* (2006.01)
*A61B 6/02* (2006.01)
*A61B 34/10* (2016.01)

(52) U.S. Cl.
CPC .............. *A61B 6/482* (2013.01); *A61B 6/505* (2013.01); *A61B 6/5217* (2013.01); *G06T 17/20* (2013.01); *A61B 6/4071* (2013.01); *A61B 6/4078* (2013.01); *A61B 34/10* (2016.02); *G06T 2207/10116* (2013.01); *G06T 2207/30008* (2013.01)

(56) References Cited

U.S. PATENT DOCUMENTS

| | | | |
|---|---|---|---|
| 9,153,021 B2* | 10/2015 | Wilson | A61B 6/466 |
| 2006/0069318 A1* | 3/2006 | Keaveny | A61B 5/4509 |
| | | | 600/300 |
| 2008/0031412 A1* | 2/2008 | Lang | G01B 15/045 |
| | | | 378/54 |
| 2011/0058649 A1* | 3/2011 | Wear | A61B 6/4042 |
| | | | 378/55 |
| 2011/0231162 A1 | 9/2011 | Ramamurthi et al. | |

* cited by examiner

Norland pencil beam

XR 600 or XR 800

Wide angle fan beam

Hologic discovery, Explorer or horizon

Narrow angle fan beam iDXA, Prodigy

SYSTEM AND METHOD FOR DXA TOMO-BASED FINITE ELEMENT ANALYSIS OF BONES

BACKGROUND OF INVENTION

Bone density or bone mineral density (BMD) is the amount of bone mineral in bone tissue. The concept is of mass of mineral per volume of bone (relating to density in the physics sense), although clinically it is measured by proxy according to optical density per square centimeter of bone surface upon imaging. Bone density measurement is used in clinical medicine as an indirect indicator of osteoporosis and fracture risk. It is measured by a procedure called densitometry, often performed in the radiology or nuclear medicine departments of hospitals or clinics. The measurement is painless and non-invasive and involves low radiation exposure. Measurements are most commonly made over the lumbar spine and over the upper part of the hip. The forearm may be scanned if the hip and lumbar spine are not accessible.

Body composition is expressed by the fraction of fatty tissue composing soft (non-mineral) tissue. Body composition is used in clinical medicine as an indirect indicator and/or as a risk factor of conditions or diseases (e.g., sarcopenia, diabetes, obesity, etc.). Densitometry is also used to assess body composition. Measurements are most commonly made over the whole body or whole body less head.

Fractures of the legs and pelvis due to falls are a significant public health problem, especially in elderly women, leading to much medical cost, inability to live independently, and even risk of death. Bone density measurements are used to screen people for osteoporosis risk and to identify those who might benefit from measures to improve bone strength.

While there are many different types of BMD tests, all are non-invasive. Most tests differ according to which bones are measured to determine the BMD result. These tests include:
  Dual-energy X-ray absorptiometry (DXA or DEXA)
  Dual X-ray Absorptiometry and Laser (DXL)
  Quantitative computed tomography (QCT)
  Quantitative ultrasound (QUS)
  Single photon absorptiometry (SPA)
  Dual photon absorptiometry (DPA)
  Digital X-ray radiogrammetry (DXR)
  Single energy X-ray absorptiometry (SERA)

DXA is currently the most widely used and works by measuring a specific bone or bones, usually the spine, hip, and wrist. The density of these bones is then compared with an average index based on age, sex, and size. The resulting comparison is used to determine risk for fractures and the stage of osteoporosis (if any) in an individual.

As illustrated in an exemplary embodiment in FIG. 1, a DXA scanner 100 includes a table 102 for supporting a patient 101 and in which is positioned an x-ray source 104 (typically composed of an x-ray generator, an x-ray tube, an x-ray filter and an x-ray collimator) that is movable with respect to the table 102 below the patient 101. In most implementations of DXA systems/scanners 100, the detector 106 is placed within the arm 108 opposite the detector 106, such that the detector 106 and source 104 are located on opposed side of the patient 101. The detector 106 is mainly one-dimensional, but can be two dimensional or other suitable dimensional configurations, and shall be moved to capture x-ray photons emitted by the x-ray source 104 and going through the patient body 101. The arm 108 moves the detector 106 and is associated with the x-ray source 104 that is moving in synch with the detector 106 on the arm 108. The arm 108 moves both the detector 106 and x-ray source 104 in a direction corresponding to the longer dimension of the DXA table 102. In DXA scanner implementing raster scan (pencil beam or fan beam), both detector 106 and x-ray source 104 can be moved in a direction perpendicular to the longer dimension of the DXA table 102 in order to scan the table 102/body 101 along its width.

In alternative embodiments, such as shown in FIG. 1, the table 102 includes an x-ray detector 106 disposed within an arm 108 spaced above the table 102 that is movable with respect to the table 102. The table 102, along with the detector 106 and the x-ray source 104 and arm 108 are operably connected to a computer system 110 that can control the operation of the x-ray source 104 and/or arm 108, and that can receive imaging data from the detector 106 resulting from x-rays from the x-ray source 104 passing through the patient 101 and striking the detector 106.

In a DXA imaging procedure, the scanner 100 moves the arm 108 and x-ray source 104 along the portion of the body of the patient 101 to be imaged in order to obtain multiple pairs (high and low energy) of two dimensional (2D) DXA images of the specified portion of the patient. The DXA scanner 100 can move the detector 106/x-ray source 104/ arm 108 along the body of the patient 101 from head to toe or along any portion of the body 101 in order to obtain the desired DXA images. Depending upon the type of beam generated by the x-ray source 104, e.g., pencil, fan or narrow fan (FIGS. 2A-2C), the x-ray source 104 and/or detector 106 and/or arm 108 can move directly along the main axis of the patient body or in a raster scan pattern in order to enable the x-ray source 104 and detector 106 to image the entire or specified portion of the body of the patient 101.

In performing the DXA imaging, the x-ray detector 106 produces dual energy (high energy (HE) and low energy (LE)) images of the specified portion of the body by detecting two different x-ray beams with different energy spectra generated by the x-ray source 104 or by detecting one x-ray beam generated from the x-ray source 104 and discriminating two different bins of energy. There are 3 main ways to implement DXA:
  Two x-ray beams of different energy spectra and a detector integrating energy deposited by the transmitted x-ray photons (photons which went through the body)
  One x-ray beam with a specific energy spectrum and a detector discriminating at least two beams of energy in the transmitted x-ray photons.
  One x-ray beam with a specific energy spectrum and a detector composed of at least 2 layers of detector elements such as the upper layer will detect preferentially low-energy photons, and the lower layer will detect preferentially high-energy photons.

One image is high energy and the other is low energy. The x-ray beams pass through the patient 101 being scanned and contact the detector 106 positioned on the scanner 100 opposite the x-ray source 104. The detector 106 is contacted by those x-rays passing through the patient 101 that are not absorbed by the patient tissue (bone and soft tissue), and thus measures the amount of x-rays that passes through the tissue from each beam. This will vary depending on the composition and the thickness of the tissue. Based on the difference between x-ray absorption of the tissue by the two beams, bone density and/or body composition can be measured.

In bone densitometry, the scan results are analyzed and reported as an average areal bone mineral density $BMD_a=BMC/A[Kg/m^2]$, where BMC is the bone mineral content [Kg] and A is the projected area [m²] of the volume containing the mixture of which bone mineral is part. The results are generally scored by two measures, the T-score and the Z-score. The Z-score denotes the difference between a measured value $BMD_a$ in an individual subject and the age-matched mean reference value normalized by the age-matched standard deviation of the population variance. The T-score is defined similarly but instead of age-matched values data from the young reference population are used. Concrete diagnostic criteria solely based on BMD have been provided by the operational definition of osteoporosis based on the T-score, developed by a working group of the WHO. The WHO (1994) definition uses areal $BMD_a$ as measured by DXA to categorize a subject into one of four groups: Normal ($BMD_a$ T-score≥−1.0); Low bone mass or osteopenia (−1.0>$BMD_a$ T-score>−2.5); Osteoporosis (−2.5≥$BMD_a$ T-score); Established osteoporosis (−2.5≥$BMD_a$ T-score and at least one osteoporotic fracture.

Use of DXA for BMD has several limitations. For example, as the calculation of bone density is only an approximation of bone strength based on the calculated mineral density of the bone, it is desirable to have an indication of the stress and/or strain on the bones at any location on the bone(s), in order to provide a more direct indicator of bone strength at those locations. One approach to provide this bone strength analysis is the combination of the DXA image with finite element analysis to provide a more detailed representation of the bone density of the patient.

To assist the DXA image/process in determining BMD, in DXA generally 2 images are produced, namely, a high-energy (HE) image and a low-energy (LE) image. The HE & LE images can be combined by software to generate one image of bone-equivalent thickness and one image of soft-tissue equivalent thickness. Other pairs of tissue-equivalent images can be derived from the HE & LE images providing a material calibration derived from data acquired on physical or simulated phantoms made of the adequate materials. In addition, it is also possible to use only one of the 2 images (HE or LE, Bone or soft-tissue). In the illustrated exemplary embodiment of FIG. 3, once the at least one 2D DXA image is obtained, using a suitable computer system 110/50 the at least one DXA image 10 can be compared with a reference database 12 of stored 2D DXA images 14 operably connected to or contained on the computer system 50 in order to locate a at least one stored 2D DXA image 14 that best approximates or is most similar to the at least one obtained 2D DXA image 10. One example of a system 50 and database 12 of this type is found in the 3D-DXA software package available from Galgo Medical SL, of Barcelona, Spain, in which the system 50 reconstructs bony structures in 3D from 2D DXA images to assess the cortical bone and trabecular macrostructure of the bone in the DXA image 10 according to a process disclosed in Humbert L, Martelli Y, Fonolla R, et al 2017 3*D-DXA; Assessing the Femoral Shape, the Trabecular Macrostructure and the Cortex in 3D from DXA images*. IEEE Trans Med Imaging 36: 27-39., which is expressly incorporated by reference herein in its entirety for all purposes. In this process, the reference database 12 includes the stored DXA images 14 and stored CT scan sets of images 18 that have previously been obtained from other patients and corresponding to DXA images 14. The stored DXA images 14 and corresponding stored CT sets of images 18 are utilized by the system 50 to construct a set of 3D finite element analysis (FEA) model 20 which is also stored in the database 12, each FEA model in association with each corresponding DXA image 14 and CT scan set of images 18 from which the model 20 was derived. When the system 50 is presented with the at least one obtained DXA image 10, the system 50 locates the 2D DXA image 14 best approximating the at least one obtained 2D DXA image 10. The system 50 then locates the FEA model 20 associated with the particular stored DXA image 14 selected as being closest to the at least one obtained DXA image 10. The system 50 then modifies the FEA model 20 based on the parameters from the at least one obtained 2D DXA image 10 in order to arrive at a modified FEA model 20' that illustrates different color-maps on the model 20' of different parameters relating to the bone imaged with the DXA scanner providing the at least one DXA image 10, including but not limited to, cortical thickness, cortical volumetric density and trabecular volumetric density, among others.

Alternatively, as shown in FIG. 4, the system 50 can be operated to compute the stored 2D DXA images 16 associated with a particular CT scan set of images 18 directly from the CT scan set of images 18. These computed 2D DXA images 16 are then compared with the at least one obtained 2D DXA image 10 in the manner described previously in order to arrive at the modified FEA model 20'.

However, while the process of obtaining the modified FEA model 20' provides additional information about the bone structure in the at least one obtained 2D DXA image 10, the process for constructing the modified FEA model 20' still has significant shortcomings in that the at least one obtained 2D DXA image 10 contains a limited amount of information that can be utilized to modify the FEA, model 20 and provide an accurate representation of the structure of the bone(s) of the patient.

Accordingly, it is desirable to provide an imaging system and method for determining bone density and other associated parameters with the capability to provide an operator with enhanced volumetric imaging capabilities, thereby improving the scan results and providing a better measurement of bone density and strength.

BRIEF DESCRIPTION OF THE INVENTION

There is a need or desire for an imaging system and associated method capable of obtaining x-ray images of the bones of a patient in order to enable the imaging system to providing an operator of the system with information concerning the stress and/or strain present in the bone(s) of the patient to assess bone strength, in addition to other information concerning the bone(s), such as BMD. The imaging system utilizes 2D dual energy DXA images obtained in a tomographic imaging process or mode in order to provide more detailed information to the operator of the bone structure of the patient. The imaging system obtains multiple 2D DXA images at different angles with regard to the patient in a single pass or multiple passes across the body of the patient. These 2D DXA images can then be utilized to reconstruct at least one set of 2D slices of the body of the patient (usually one (bone thickness) or two (HE/LE, bone/soft-tissue)) in planes usually parallel to the plane of the detector. The technical effect of the information provided by the tomographic reconstruction provides enhancements to the determination of the corresponding stored DXA images in a reference database and for the modification of the 3D FEA model corresponding to the at least one selected stored 2D DXA image for analysis of the structure of the bone(s)/bone tissue of the patient/individual. In this manner, the system and method provide a significant reduction in the error of the resulting modified 3D FEA model for review and analysis.

According to another aspect of the invention, a method for the analysis of bone tissue within a patient including the steps of providing a scanning device including at least one x-ray source, at least one x-ray detector and a controller for controlling the movement of the at least one x-ray source and receiving image data from the at least one detector, operating the at least one x-ray source along at least one plane relative to the patient to obtain a number of dual-energy x-ray images corresponding to the number of points, each point being located at a different angle relative to an axis perpendicular to a detecting surface of the at least one detector, reconstructing at least one two-dimensional (2D) planar slice image of the bone tissue of the patient utilizing the number of dual-energy x-ray images and modifying a finite element analysis (FEA) model with information provided by the at least one 2D planar slice image.

According to still another aspect of the invention, a method of determining various parameters of a bone within the body of a patient including the steps of providing a scanning device including at least one x-ray source, at least one x-ray detector and a controller for controlling the movement of the at least one x-ray source and receiving image data from the at least one detector operating the at least one x-ray source at a number of points along at least one plane relative to the patient to obtain a number of dual-energy x-ray images corresponding to the number of points, each point being located at a different angle relative to an axis perpendicular to a detecting surface of the at least one detector, reconstructing at least one two-dimensional (2D) planar slice image of the patient utilizing the number of dual-energy x-ray images, comparing the at least one 2D planar slice image with a database of images operably connected to the controller and modifying a finite element analysis (FEA) model with information provided by the at least one 2D planar slice image.

According to still a further aspect of the invention, a method of determining various parameters of a patient including the steps of providing a scanning device including at least one x-ray source, at least one x-ray detector and a controller for controlling the movement of the at least one x-ray source and receiving image data from the at least one detector, operating the at least one x-ray source along at least one plane relative to the patient to obtain a number of dual-energy x-ray images corresponding to the number of points, each point being located at a different angle relative to an axis perpendicular to a detecting surface of the at least one detector, reconstructing at least one two-dimensional (2D) planar slice image of the patient utilizing the number of dual-energy x-ray images, segmenting the at least one 2D slice image into bone pixels and tissue pixels and measuring tissue mass in tissue pixels and tissue and bone mass in bone pixels.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
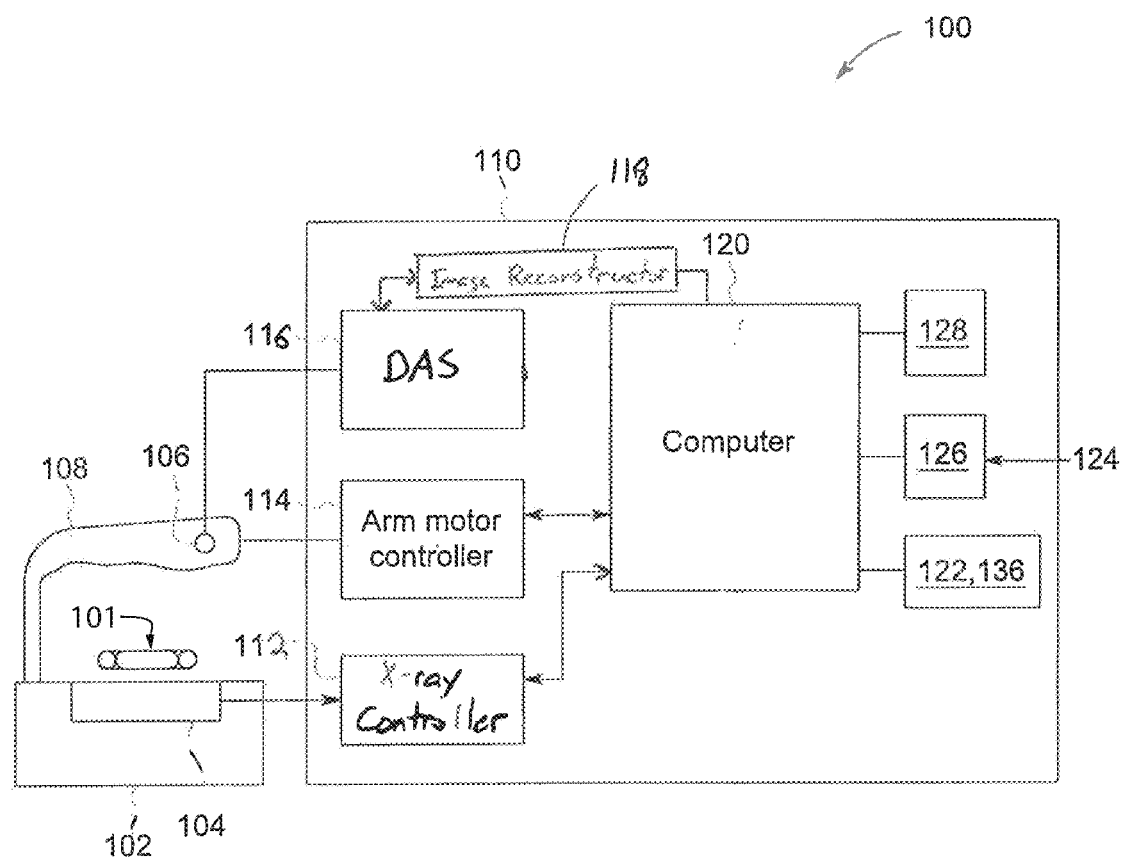
FIG. 1 is a schematic representation of a DXA imaging system according to an exemplary embodiment of the invention.

Referring now to FIG. 1, a dual-energy x-ray absorptiometry (DXA) imaging system and/or scanner 100 is illustrated in accordance with one exemplary embodiment of the invention. As described previously, the DXA scanner 100 includes a table 102 for supporting a patient 101 and in which is positioned an x-ray source 104 below the patient 101. The table 102 also includes an x-ray detector 106 disposed within an arm 108 spaced above the table 102 that is movable with respect to the table 102. The positions of the x-ray source 104 and the detector 106 can also be reversed, as desired. The table 102, along with the detector 106 and the x-ray source 104 and arm 108 are operably connected to a computer system 110 that can control the operation of the x-ray source 104 and/or arm 108, and that can receive imaging data from the detector 106 resulting from x-rays from the x-ray source 104 passing through the patient 101 and striking the detector 106.

Figure 5:
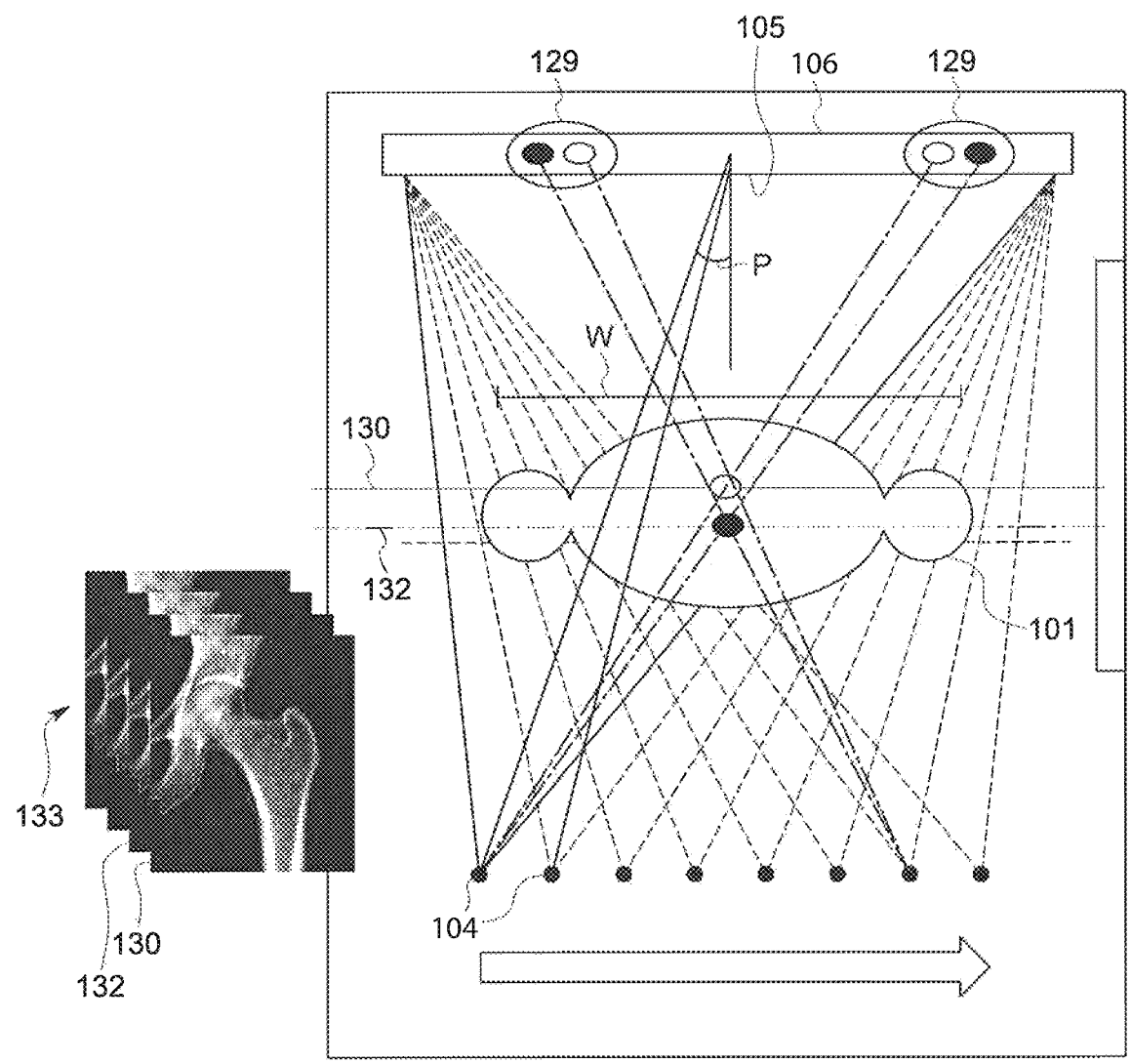
FIG. 5 is a schematic view of a scanning method using the DXA imaging system of FIG. 1 according to one embodiment of the invention.

Looking at FIGS. 1 and 5, in performing the scan to acquire x-ray projection data, the movement of the arm 108 and the operation of the x-ray source 104 and/or the detector 106 are governed by the control mechanism/computer system 110 of the DXA scanner 100. The control mechanism 110 includes an x-ray controller 112 that provides power and timing signals to the x-ray source 106 and an arm motor controller 114 that controls the speed and position of the arm 108. A data acquisition system (DAS) 116 in the control mechanism 110 samples analog data from the detector 106, when the detector does not deliver direct digital signals, and converts the data to digital signals for subsequent processing, An image reconstructor 118 receives sampled and digitized x-ray data from the DAS 116 and performs high-speed reconstruction. The reconstructed image is applied as an input to a computer 120, which stores the image in a database/mass storage device 122.

Moreover, the computer 120 also receives commands and scanning parameters from an operator via operator console 124 that may have an input device such as a keyboard 126. An associated display 128 allows the operator to observe the reconstructed image and other data from the computer 120. Commands and parameters supplied by the operator are used by the computer 120 to provide control and signal information to the DAS 116, the x-ray controller 112 and the arm motor controller 114.

Looking now specifically at FIG. 5, in one exemplary embodiment of the invention, the movement of the x-ray source 104 is schematically shown with respect to the patient 101 and the detector(s) 106 during a head-to-toe scan of the patient 101. As opposed to the prior art scanning paths illustrated in FIGS. 2A-2C, the scanner 100 can be operated in varying tomographic imaging scan modes, such as in a raster scan with the x-ray source 104 moving at least in part along a plane perpendicular to the detector 106, in a scan where the x-ray source 104 is moving at least in part in a continuous motion, where limited x-ray exposures in time will produce different dual energy projections of the imaged object, and/or where the x-ray source 104 is moving at least in part perpendicular to plane P, but in a more complex movement pattern other than simply planar, and optionally at varying distances to the detector 106, in order to enable optimization of the image quality when reconstructing tomosynthesis data from the set of projections acquired under different angles. In the illustrated exemplary embodiment of FIG. 5, the x-ray source 104 is moved along a plane or section W of the patient 101 oriented parallel to the entrance or detection surface 105 of the detector 106 and is stopped and operated at a number of locations at varying angles between the axis going through the x-ray source 104 and the center of the detector 106 and the axis P at the center of and perpendicular to the detection surface 105 of the at least one detector 106. Once a desired number of images 129 have been obtained at that particular section W of the patient 101, the arm 108 moves the source 104 and/or detector 106 to a different and potentially overlapping section W in order to obtain additional images 129. This process is repeated a number of times until the patient 101 has been adequately scanned over their entire body or specified part of the body. The multiple imaging positions for the x-ray source 104 enable the x-ray source 104 to produce or obtain multiple images 129 on the detector 106 of the same objects (e.g., bones) within the patient 101 at different angles relative to the plane P, where the images 129 can be dual energy images, i.e., low and high energy images obtained of the patient 101 at each location at which the x-ray source 104 is operated. In the DAS 116 and image reconstructor 118, these images 129 can be tomographically reconstructed to form at least one set of 2D images 130, 132 at different heights within the patient 101 that are parallel or at other desired orientations relative to the detector 106.

In an alternative exemplary embodiment, the scanner 100 can include multiple x-ray sources 104 that are spaced from one another along the arm 108. In operation, the individual x-ray sources 104 are sequentially operated in order to generate the dual energy images 129 for tomographic reconstruction into the set 133 of 2D plane images 130,132, but without movement of the x-ray sources 104 being operated within a given plane perpendicular to the entrance surface of the detector 106. As such, the presence and operation of the multiple sources 104 can eliminate any mechanical-induced variation in the dual energy images 129 obtained between the sources 104, as the sources 104 remain stationary during the process for obtaining each of the dual energy images 129.

Figure 6:
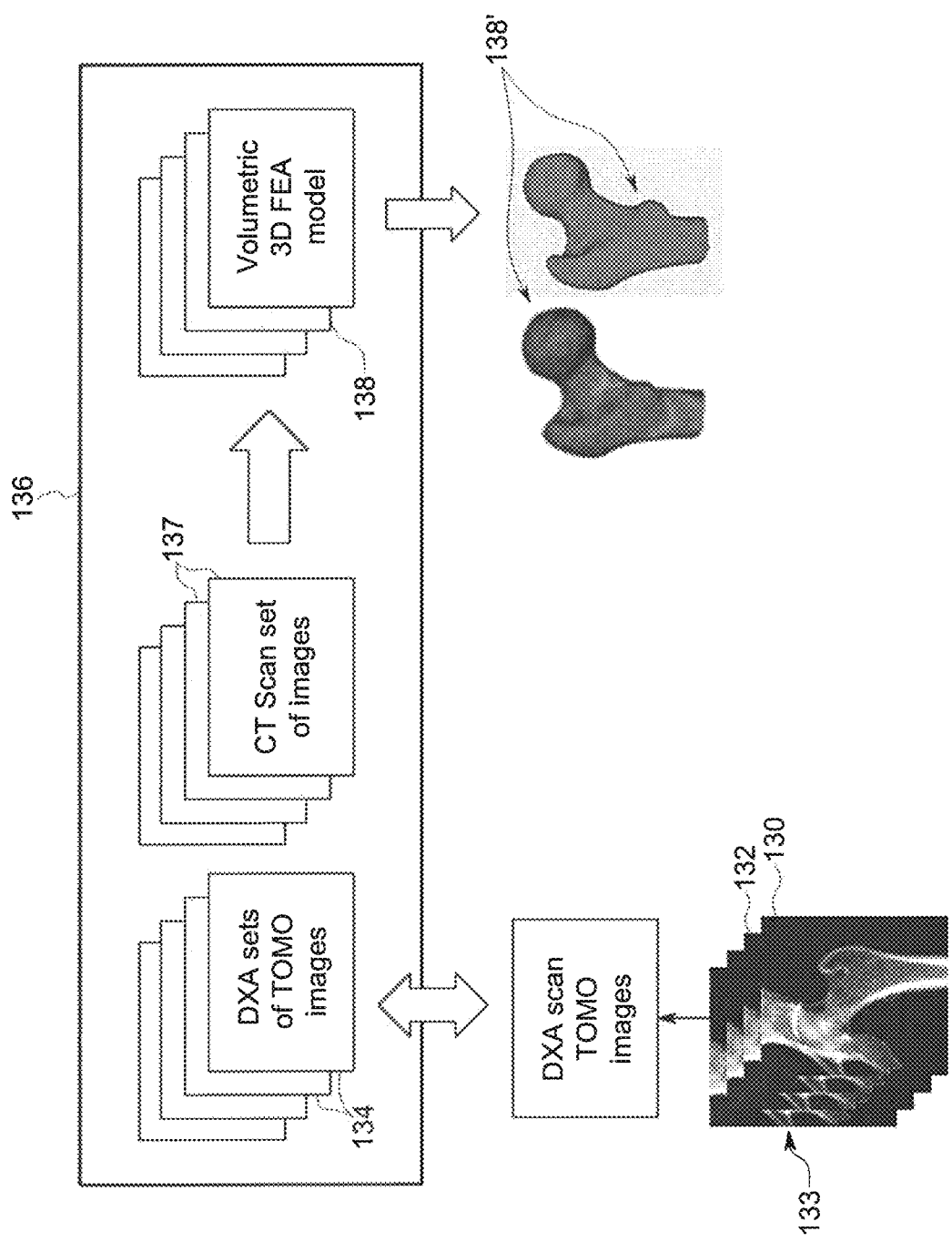
FIG. 6 is a block schematic diagram of one embodiment of an image analysis system utilized in conjunction with the scanning method of FIG. 5.

Referring now to the exemplary embodiment illustrated in FIG. 6, after completing the reconstruction of the at least one set 133 of planar images 130,132, these images 130,132 can individually or collectively be compared with one or more stored sets of 2D tomographic scan images 134 obtained from DXA scans of other patients that are retained within a database 122,136 operably connected to the control mechanism 110. When a close comparison is made or similarity is found between the one or more of the obtained 2D tomographic images 130 and 132 in the set 133 and one or more of the stored 2D tomographic images in a DXA scan set of TOMO images 134, the control mechanism 110 can access the CT scan set of images 137 stored in the database 122,136 in association with the particular stored DXA scan set of tomographic images 134 in order to generate or locate a stored 3D finite element analysis (FEA) model 138 relating to the selected stored sets of images 134 and 137. In the generation of, or as a modification to the model 138, the information from the set 133 of obtained DXA tomographic images 130,132 is included in the FEA model 138 to construct the model 138' which can be subsequently illustrated on the display 128 or other similar device operably connected to the scanner 100. In this manner, the additional information provided by the at least one DXA tomographic image set 133 significantly reduces errors in the construction of the model 138 and in the representation of the color maps of different parameters displayed on the model 138', such as cortical thickness, cortical volumetric density and trabecular volumetric density of the bone, among others, and/or assessment of risk of fracture provided on or by the model 138.

Figure 7:
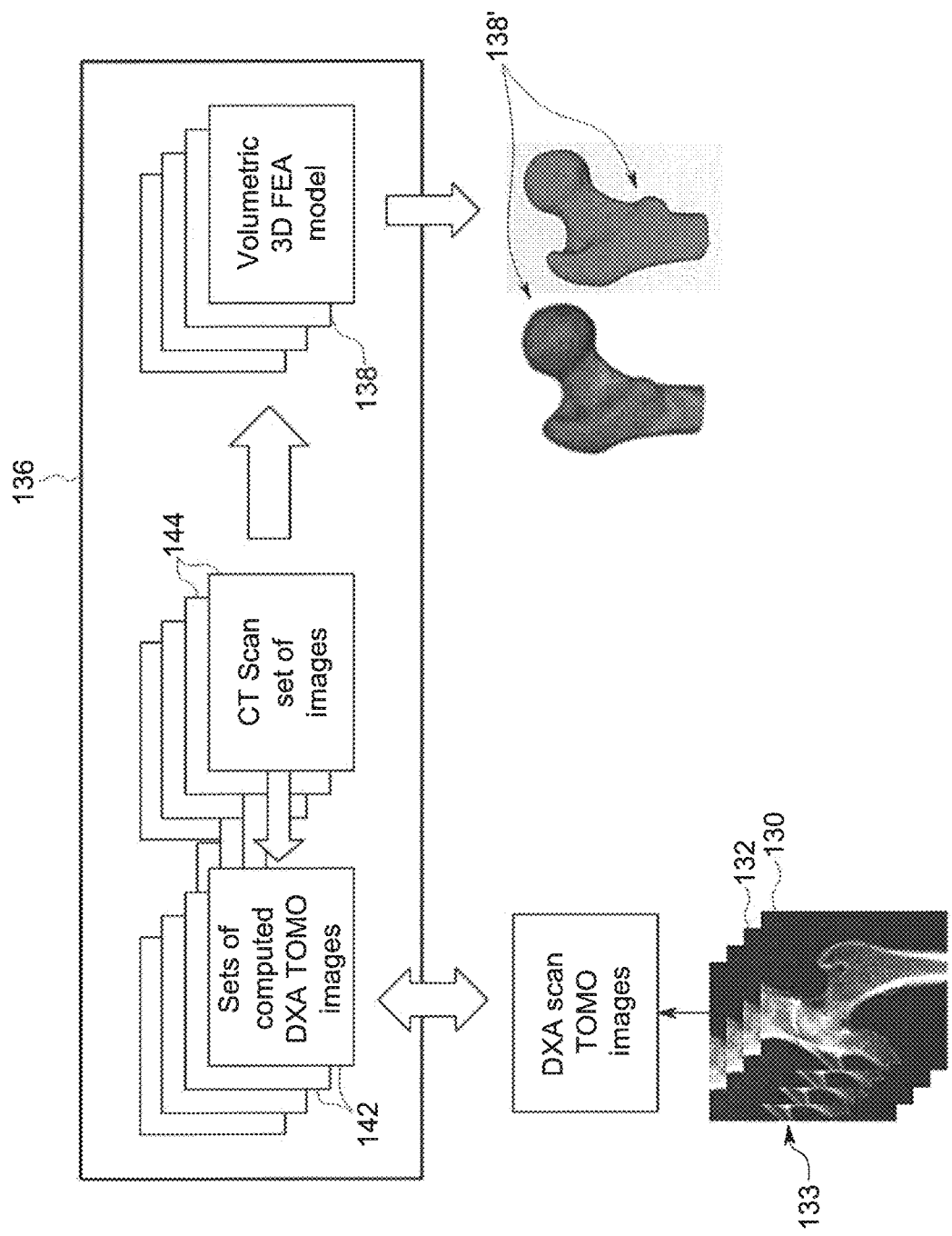
FIG. 7 is a block schematic diagram of one embodiment of an image analysis system utilized in conjunction with the scanning method of FIG. 5.

Looking now at FIG. 7, in an alternative embodiment of the invention, the at least one obtained set 133 of DXA tomographic images 130,132 is compared with stored sets of computed DXA tomographic images 142 located in the database 122,136. These sets of computed DXA tomographic images 142 are reconstructed from sets of CT scan images 144 of prior patients that are stored in the database 136 for comparison with the at least one set 133 of obtained DXA tomographic images 130,132 and for the formation of the FEA models 138 with the stored set of CT scan images 144 and the information from the obtained DXA scan tomographic images 130,132. In this exemplary embodiment, no prior DXA scans are conducted on other patients, as the DXA images 142 compared with the obtained sets 133 of DXA scan tomographic images 130,132 are reconstructed directly from CT scan images 144 of the patients, which are used to construct the models 138.

Figure 8:
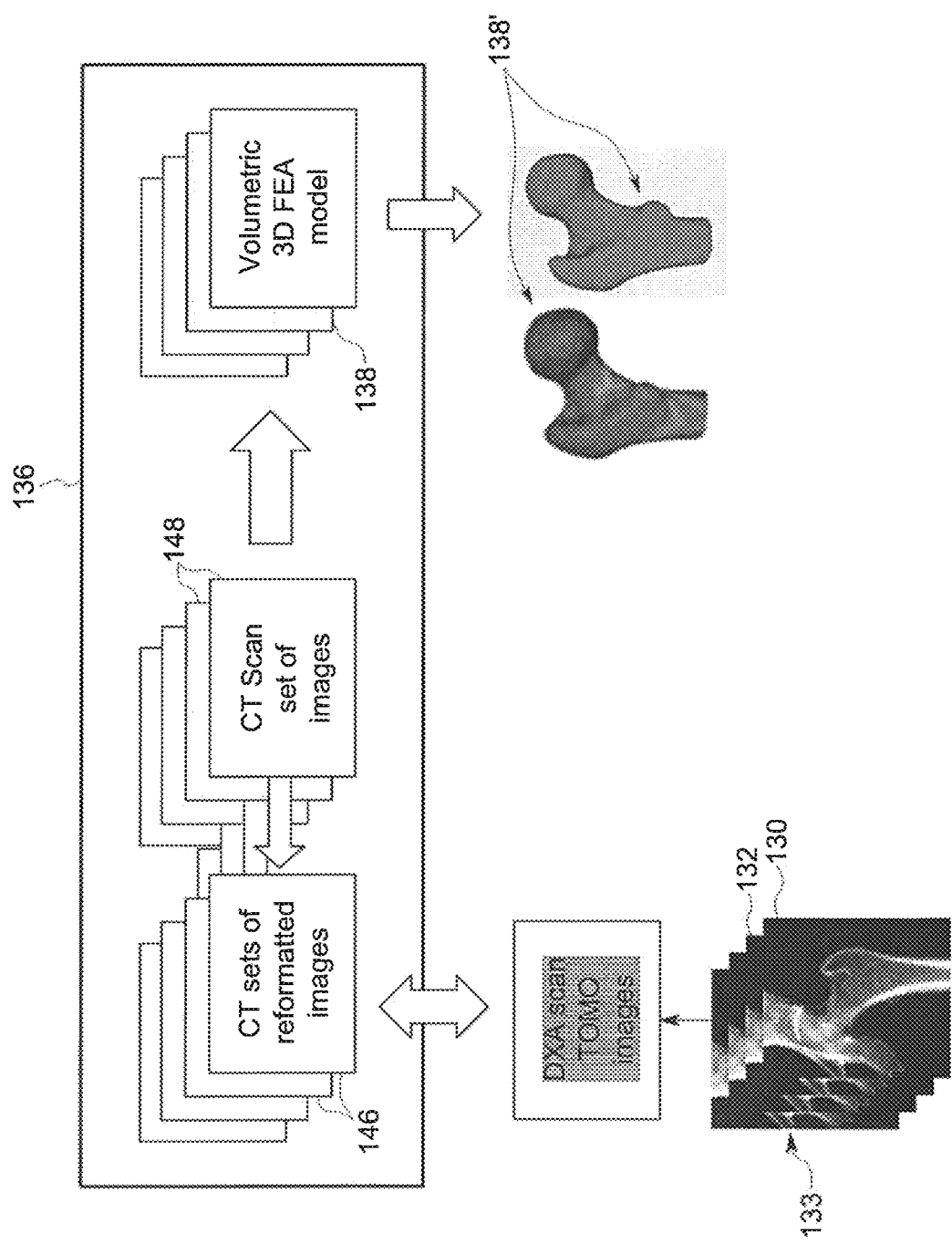
FIG. 8 is a block schematic diagram of one embodiment of an image analysis system utilized in conjunction with the scanning method of FIG. 5, FIGS. 9A-9B are block schematic diagrams of a prior art body composition image analysis system and one embodiment of an image analysis system utilized to determine body composition in conjunction with the scanning method of FIG. 5.

In another exemplary embodiment of the invention illustrated in FIG. 8, the at least one set 133 of obtained DXA scan tomographic images 130,132 is compared with reformatted sets of CT scan images 146 constructed from sets of CT scan images 148 taken of prior patients and stored in database 122,136. The reformatted sets of CT scan images 146 are images reconstructed from the sets of CT scan images 148 that correspond to the image planes for the at least one obtained DXA scan tomographic images 130,132, such as along the various coronal plane of the patient. The selected reformatted images 146 are then utilized in conjunction with the CT scan images 148 and the information from the at least one set 133 of obtained DXA scan tomographic images 130,132 to generate the FEA model 138.

Figure 2A:
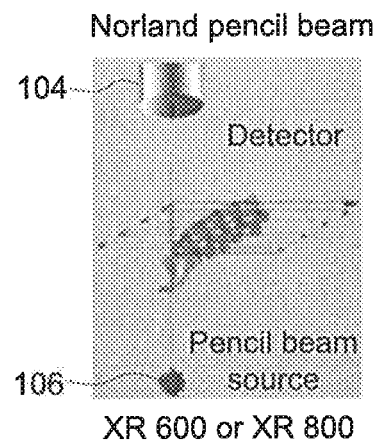
FIGS. 2A-2C are schematic views of the scanning geometries for the DXA imaging system of FIG. 1.
Figure 2B:
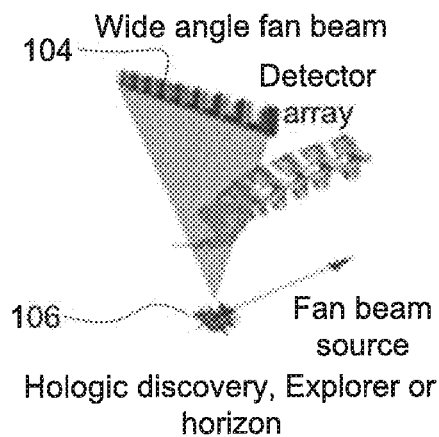
Figure 2C:
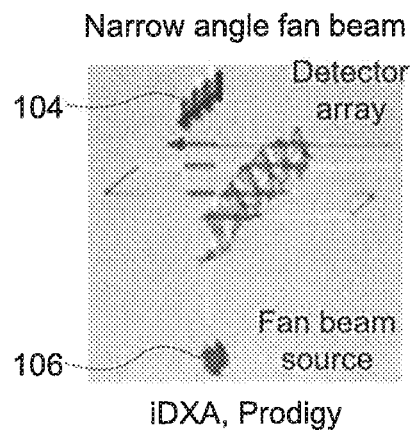
Figure 3:
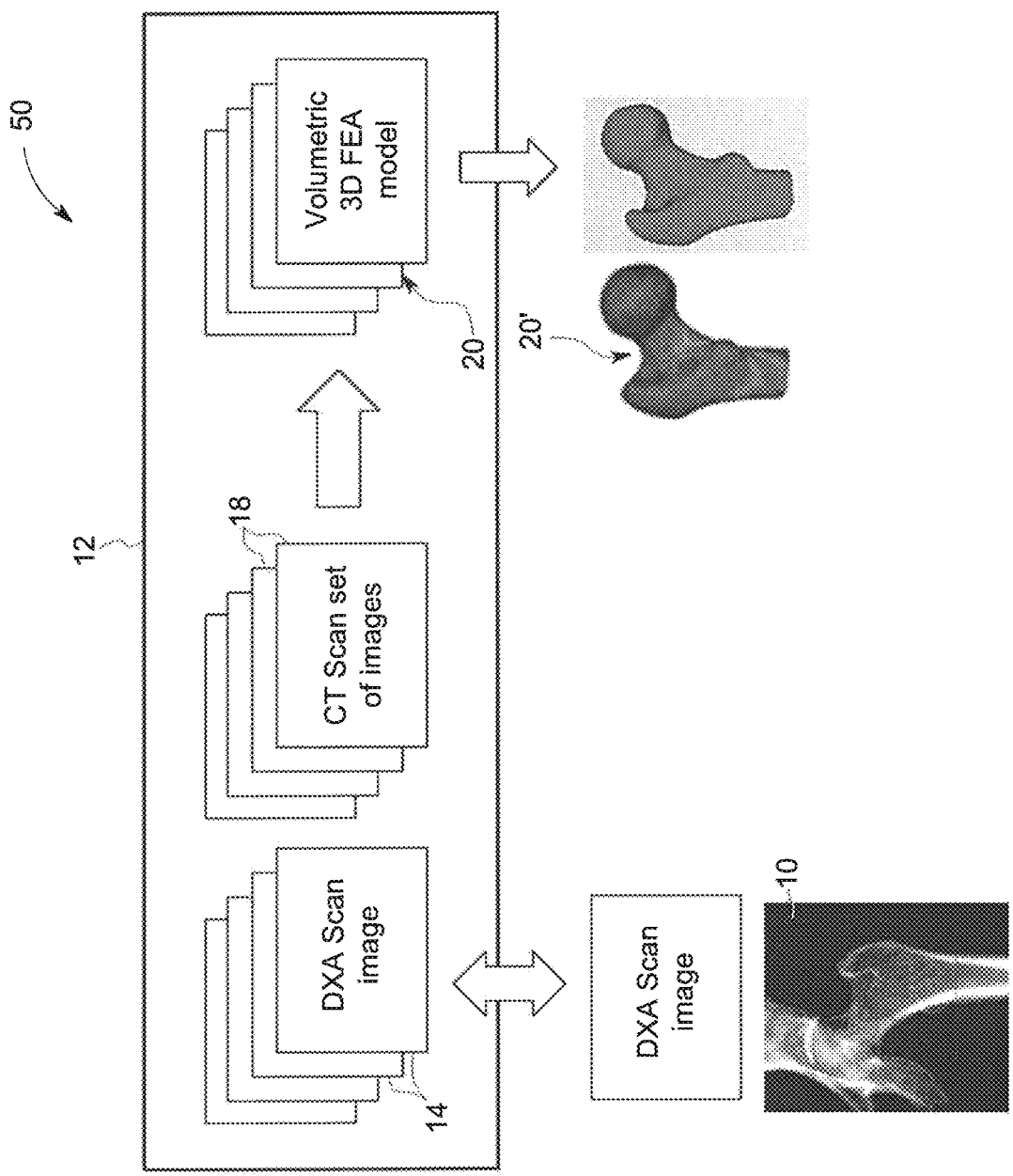
FIG. 3 is a block schematic diagram of a prior art image analysis system utilized in conjunction with the DXA imaging system illustrated in FIG. 1.
Figure 4:
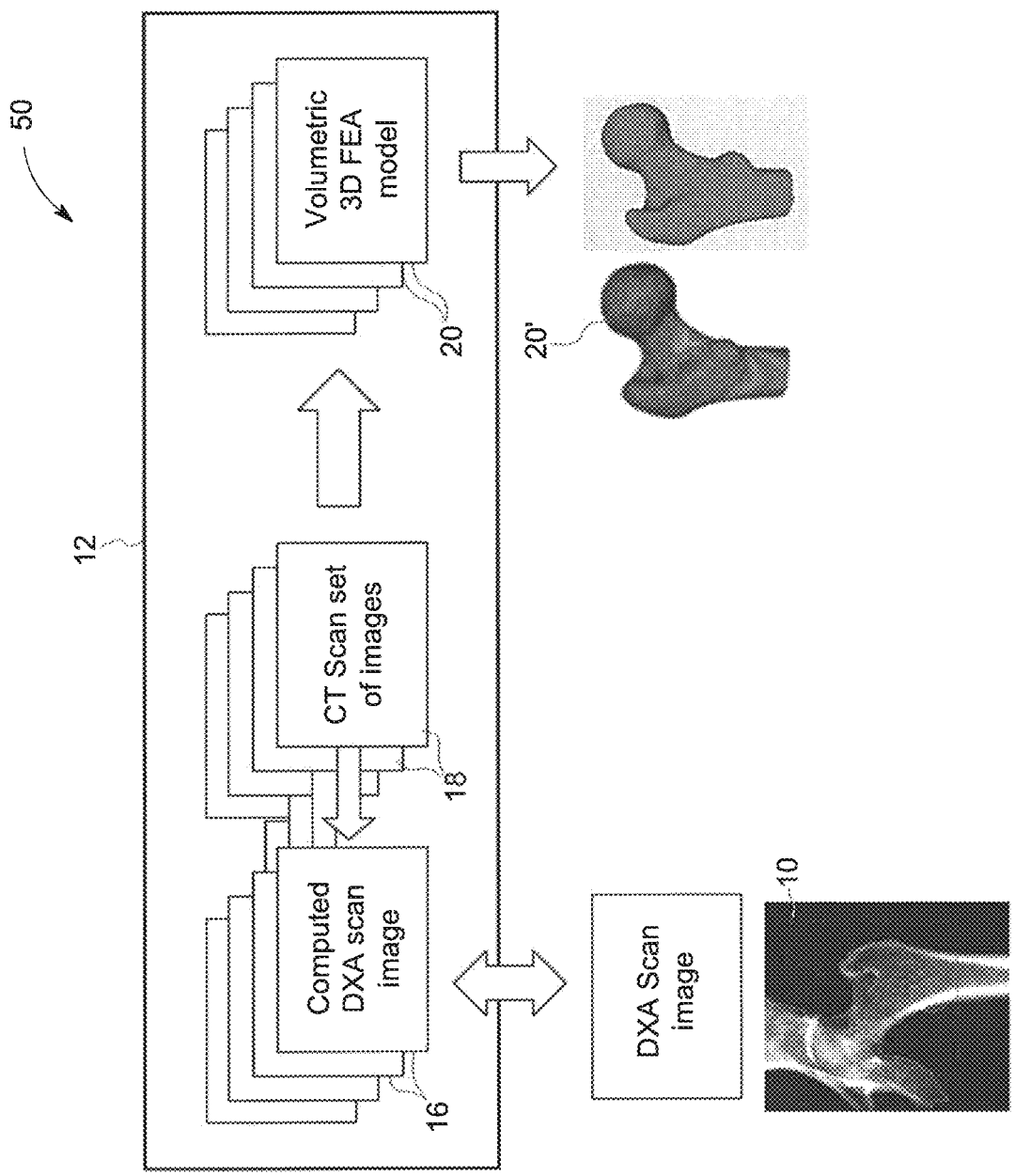
FIG. 4 is a block schematic diagram of a prior art image analysis system utilized in conjunction with the DXA imaging system illustrated in FIG. 1.
Figure 9A:
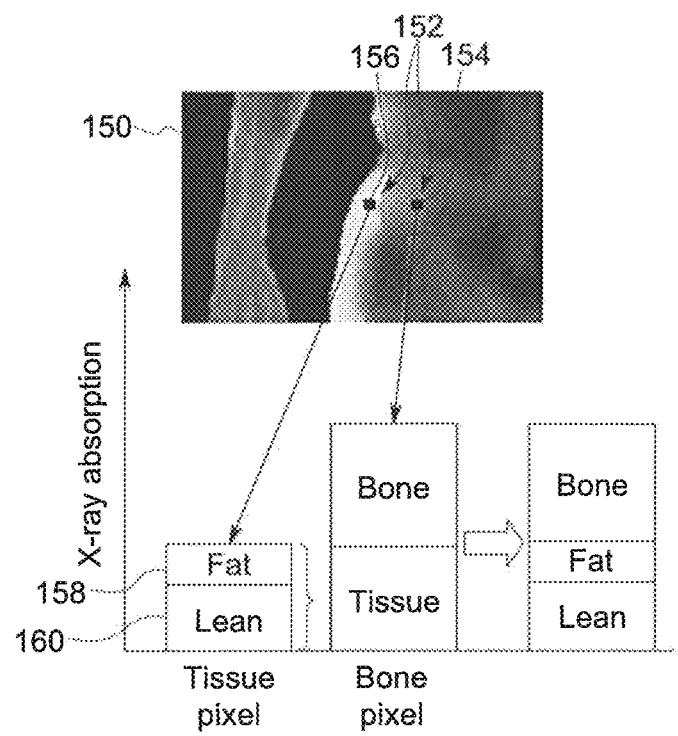

Referring now to FIG. 9A, a DXA scan image 150 is illustrated as obtained using a DXA scanner 10 and a scanning method illustrated in one of FIGS. 2A-2C. In the image 150, each pixel 152 is analyzed based on whether the pixel 152 is a bone pixel 154 or a soft tissue pixel 156, constituted of fat tissue 158 and/or lean tissue 160 (muscle, non-fat and non-mineral tissue). In a soft tissue pixel 156, the analysis measures the fat tissue fraction 158 and the lean tissue fraction 160 from the combination of low-energy and high-energy DXA images. However, in the bone pixels 154, due to the inability to derive the fraction of three different materials (fat, lean and bone) from only two images acquired at two different energies, it is assumed that the soft tissue composition within the bone pixel 154 is similar to the soft tissue composition in neighborhood soft tissue pixel 156, and the bone, fat and lean tissue fractions are derived accordingly. Once the analysis is complete, the values for the bone tissue fraction, fat tissue fraction 158 and lean tissue fraction 160 are added over the total body of the individual being scanned and over the region of interest.

Figure 9B:
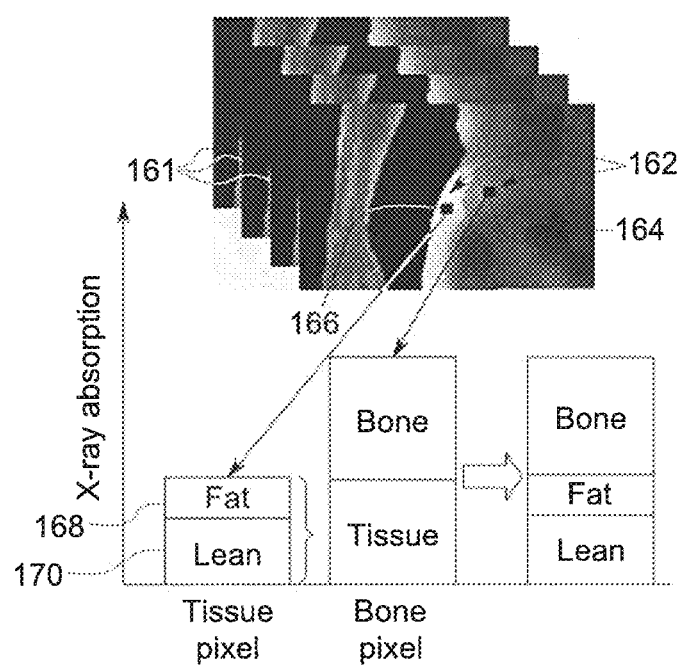

Looking now at FIG. 9B, in another exemplary embodiment of the invention a body composition measurement is performed utilizing a DXA scanner 100 and associated tomographic scanning method as illustrated schematically in FIG. 5 to obtain a number of 2D tomographic slices 161 of the body or region of interest within the body. As a result, while the individual pixels 162 in each of the tomographic images/slices 161 are similarly segmented into bone pixels 164 and soft tissue pixels 166, the quantification of the fat tissue fraction 168 and the lean tissue fraction 170 is more accurate due to the volumetric assessment of the fat tissue fraction 168 and lean tissue fraction 170 that can be performed in each slice 160, with a consequently more accurate result obtained from the combination of the results of each slice 161.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for the analysis of bone tissue within a patient, the method comprising the steps of:
    providing a scanning device including at least one x-ray source, at least one x-ray detector and a controller for controlling the movement of the at least one x-ray source and receiving image data from the at least one detector;
    operating the at least one x-ray source at a number of points along at least one plane relative to the patient to obtain a number of dual-energy x-ray images corresponding to the number of points, each point being located at a different angle relative to an axis perpendicular to a detecting surface of the at least one detector;
    reconstructing at least one two-dimensional (2D) planar slice image of the bone tissue of the patient utilizing the number of dual-energy x-ray images; and
    modifying a finite element analysis (FEA) model with information provided by the at least one 2D planar slice image.

2. The method of claim 1, wherein the step of operating the at least one x-ray source comprises:
    emitting x-rays from the at least one x-ray source at a first position relative to the detector to produce a first dual energy x-ray image;
    moving the at least one x-ray source from the first position relative to the detector to a second position; relative to the detector and
    emitting x-rays from the at least one x-ray source at the second position relative to the detector to produce a second dual energy x-ray image.

3. The method of claim 1, wherein the step of operating the at least one x-ray source comprises:
    emitting x-rays from a first x-ray source at a first position relative to the detector to produce a first dual energy x-ray image; and
    emitting x-rays from a second x-ray source at a second position spaced from the first x-ray source at the first position to produce a second dual energy x-ray image.

4. The method of claim 1, wherein the step of operating the at least one x-ray source comprises:
    emitting x-rays from the at least one x-ray source to produce a first number of dual energy x-ray images along a first width of the patient;
    moving the x-ray source to a second width of the patient spaced from the first width; and
    emitting x-rays from the at least one x-ray source to produce a second number of dual energy x-ray images along the second width of the patient.

5. The method of claim 4, wherein the step of reconstructing the at least one two dimensional (2D) planar slice image comprises:
    tomographically reconstructing a first 2D slice from the first and the second number of dual energy x-ray images; and
    tomographically reconstructing a second 2D slice from the first and the second number of dual energy x-ray images.

6. A method of determining various parameters of a bone within the body of a patient, the method comprising the steps of:
    providing a scanning device including at least one x-ray source, at least one x-ray detector and a controller for controlling the movement of the at least one x-ray source and receiving image data from the at least one detector;
    operating the at least one x-ray source at a number of points along at least one plane relative to the patient to obtain a number of dual-energy x-ray images corresponding to the number of points, each point being located at a different angle relative to an axis perpendicular to a detecting surface of the at least one detector;
    reconstructing at least one two-dimensional (2D) planar slice image of the patient utilizing the number of dual-energy x-ray images;
    comparing the at least one 2D planar slice image with a database of images operably connected to the controller; and modifying a finite element analysis (FEA) model with information provided by the at least one 2D planar slice image.

7. The method of claim 6 wherein the database of images comprises a database of reconstructed 2D planar slice images.

8. The method of claim 6 wherein the database of images comprises a database of reconstructed 2D planar slice images reconstructed from CT scan images.

9. The method of claim 6 wherein the database of images comprises a database of reformatted CT scan images.

10. The method of claim 6 further comprising the steps of:
selecting one of the database images; and
modifying a finite element analysis (FEA) model associated with the selected database image using the reconstructed 2D planar slice image.

11. The method of claim 10 wherein the step of modifying the FEA model comprises altering a parameter represented on the FEA model.

12. The method of claim 11 wherein the step of altering the parameter comprises altering a representation of the parameter on the FEA model.

13. The method of claim 12 wherein the step of altering the representation of the parameter comprises altering a color map provided on the FEA model.

14. The method of claim 11 wherein the parameter is selected from the group consisting of: cortical thickness of a bone, cortical volumetric density of a bone, and trabecular volumetric density of a bone.

15. The method of claim 10 further comprising the step of forming the FEA model with the selected database image and a CT scan image stored in the database in association with the selected database image prior to modifying the FEA model.

16. The method of claim 10 wherein the FEA model is stored in the database in association with the selected image.

* * * * *